United States Patent [19]
Shain et al.

[11] Patent Number: 6,009,343
[45] Date of Patent: *Dec. 28, 1999

[54] ENHANCED TRANSDERMAL TRANSPORT OF FLUID USING VACUUM

[75] Inventors: Eric B. Shain, Glencoe; Tuan A. Elstrom, Lake Bluff, both of Ill.; Thomas G. Schapira, Bristol, Wis.; Timothy P. Henning, Vernon Hills, Ill.

[73] Assignee: Abbott Laboratories, Abbott Park, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/606,506

[22] Filed: Feb. 23, 1996

[51] Int. Cl.$^6$ ........................................ A61N 1/30
[52] U.S. Cl. ................................. 604/20; 604/22; 601/2
[58] Field of Search ................ 604/20–22, 289, 604/290, 313; 128/760, 771, 632, 633, 637, 638; 601/2; 607/149

[56] References Cited

U.S. PATENT DOCUMENTS

| | | |
|---|---|---|
| 4,767,402 | 8/1988 | Kost et al. . |
| 4,780,212 | 10/1988 | Kost et al. . |
| 5,115,805 | 5/1992 | Bommannan et al. . |
| 5,161,532 | 11/1992 | Joseph . |
| 5,171,215 | 12/1992 | Flanagan . |
| 5,421,816 | 6/1995 | Lipkovker . |
| 5,458,140 | 10/1995 | Eppstein et al. . |

FOREIGN PATENT DOCUMENTS

| | | |
|---|---|---|
| 513789 | 11/1992 | European Pat. Off. . |
| 595237 | 5/1994 | European Pat. Off. . |

OTHER PUBLICATIONS

S. Mitragotri, et al, "A Mechanistic Study of Ultrasonically–Enhanced Transdermal Drug Delivery", *Journal of Pharmaceutical Sciences*, vol. 84, No. 6, Jun. 1995, pp. 697–705.
Patent Application No. 08/563,728, filed Dec. 18, 1995, to Timothy P. Henning, et al. for "Interference Free Biosensor".
Patent Application No. 08/573,805, filed Dec. 18, 1995, to Timothy P. Henning, et al., for "Pump for Use in Non–Invasive or Minimally Invasive Detection of Analytes".
Patent Application No. 08/606,109, filed Feb. 23, 1996, to Tuan A. Elstrom, et al. for "Transdermal Transport Using Ultrasonic Standing Waves".

*Primary Examiner*—Corrine McDermott
*Assistant Examiner*—David J. Cho
*Attorney, Agent, or Firm*—David L. Weinstein; Gregory W. Steele

[57] ABSTRACT

The present disclosure provides the use of vacuum to enhance the transdermal transport of fluids in sampling methods for the detection of analytes in a patient's blood.

11 Claims, 2 Drawing Sheets

ENHANCED TRANSDERMAL TRANSPORT OF FLUID USING VACUUM

FIELD OF THE INVENTION

The present disclosure relates to improved sampling methods for the detection of analytes in a patient's blood. More specifically, the invention is related to the use of vacuum to enhance the transdermal transport of fluids.

BACKGROUND OF THE INVENTION

The ability to accurately measure analytes in the blood, particularly glucose, is important in the management of diseases such as diabetes. Blood glucose levels must be maintained within a narrow range (about 3.5–6.5 mM). Glucose levels lower than this range (hypoglycemia) may lead to mental confusion, coma, or death. High glucose levels (hyperglycemia) cause excessive thirst and frequent urination. Sustained hyperglycemia has been linked to several of the complications of diabetes, such as kidney damage, neural damage, and blindness.

Blood glucose levels are maintained in many diabetics with routine injections of insulin. Unlike the normal functioning of the body's glucose control systems, injections of insulin incorporate no feedback mechanisms. Controlling glucose levels therefore requires continuous or frequent measurements of blood glucose concentration in order to determine the proper amount and frequency of insulin injections.

Conventional glucose measurement techniques require lancing of a convenient part of the body (normally a fingertip) with a lancet, milking the finger to produce a drop of blood at the impalement site, and depositing the drop of blood on a measurement device (such as an analysis strip). This lancing of the finger, at typical measurement frequencies of two to four times a day, is both painful and messy for the patient. The pain and inconvenience has additional and more serious implications of noncompliance, in that many patients will not maintain the recommended regimen of blood glucose measurement and thereby run the risk of improper glucose levels and consequent harmful effects.

In short, the inherent limitations of conventional blood glucose measurement techniques mean that patients either suffer this pain and inconvenience or neglect glucose monitoring and suffer the adverse physiological effects of improper glucose control. There is a clear need for a glucose measurement technique that minimizes or eliminates pain and inconvenience to the patient.

Devices have been described which use a pump to draw body fluid from the patient to a glucose detector or other analytical instrument. For example, U.S. Pat. No. 5,161,532 uses a pump to draw interstitial fluid from the skin to an integral glucose sensor. This system requires a pump capable of creating, suction at a level of about 200–400 mmHg. EP Publication 0 595 237 discloses an analytical device for measuring blood constituents such as glucose, which also requires a suction pump capable of creating, suction at a level of about 400 mmHg. Body fluid is also sampled through the skin with a suction pump in EP Publication 0 513 789.

In addition, devices have been described which use the local application of ultrasound to increase the permeability of the skin. Ultrasound is believed to disrupt the lipid layers between the keratinocytes in the stratum corneum, thereby increasing the permeability of the skin (Mitragotri et al, *J. Pharm Sci* 84:697–706, 1995). U.S. Pat. Nos. 4,767,402, 4,780,212, 5,115,805, and 5,421,816 discuss the application of frequency and/or modulation of ultrasound to increase the permeability of skin for the purposes of drug, delivery.

There remains a need for improved devices and methods for the application of a static pressure gradient to increase the effectiveness of ultrasound enhanced permeability, particularly with the objective of enabling, speed of extraction while minimizing tissue damage, better control of rates of extraction, and rapid and minimally invasive sampling of body analytes such as glucose.

SUMMARY OF THE INVENTION

The present invention provides a process of sampling extracellular fluid from the skin of an animal wherein ultrasound is applied to a region of the skin, reduced pressure is applied to the same vicinity of the skin and any fluid which exudes the skin is collected. The application of ultrasound and reduced pressure may be performed either sequentially or simultaneously. A preferred source of ultrasound is a standing wave. A preferred analyte is glucose.

The present invention also provides a device for the transdermal sampling, of extracellular fluid comprising a means for generating an ultrasonic wave through skin of an animal, means for applying reduced pressure to the external surface of the skin in the vicinity of the ultrasonic wave, and means for collecting fluid that transudates the skin. A preferred device utilizes an ultrasonic standing, wave and incorporates an analysis element for the analysis of the fluid collected. A preferred analyte for collection by the device of the invention is glucose.

The present invention also provides an improved apparatus for the sampling of extracellular fluid across the skin of animal comprising the application of reduced pressure to the external surface of the skin in the vicinity of the ultrasonic wave.

DETAILED DESCRIPTION OF THE INVENTION

The term "analyte" means any chemical or elemental compound of clinical and/or medical, environmental, or industrial significance and for which quantitative or qualitative measurements may be desired. Examples of specific analytes are well known and include analytes of clinical significance such as glucose, hemoglobin, lipids, cholesterol, proteins, etc. Other analytes will be readily apparent to those skilled in the art. A preferred biological compound is glucose.

Figure 1:
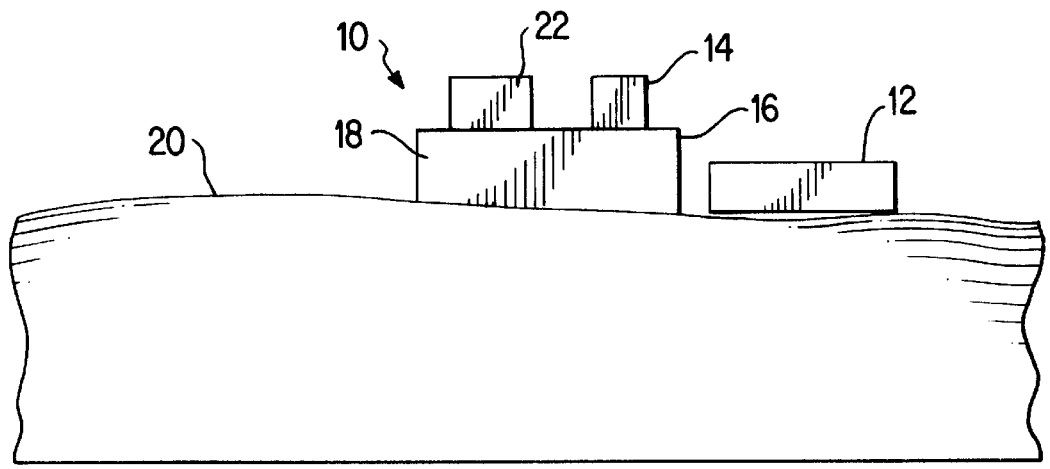
FIG. 1 shows one embodiment of the invention.

The present disclosure provides an apparatus and method for enhancing the transdermal transport of analytes. As illustrated in FIG. 1, an apparatus of the invention generally consists of a sampling device 10 comprising a ultrasonic source 12, a pressure reducing source 14, a pressure boundary 16 which, together with a surface 20 of a body part, contains a sampling region 18, and an analysis device 22. Any ultrasonic source 12 is suitable for use in the present invention. Preferably, the source is an ultrasonic transducer capable of generating ultrasonic energy at a frequency range suitable for optimum extraction of glucose, e.g., 20 KHz to 1 MHz. The pressure reducing source 14 is capable of reducing pressure in the sampling, region 18 to an absolute pressure of about 400 mmHg, a vacuum pump is preferred. In one embodiment, the pump is powered by normal movements, such as the self-actuated pump described in U.S. patent application Ser. No. (not yet available; Atty Docket Number 5845.US.01, filed Dec. 18, 1995). The pressure boundary 16 maintains a pneumatic seal against the surface 20 of the body, and may be any of a variety of well known materials suitable for this purpose, e.g.,., adhesive tape or an elastomeric ring. In those embodiments where analysis of analyte in sampling region 18 is provided, analysis of collected sample is provided by analysis element 22 located adjacent or, as shown in FIG. 1, in contact with sampling region 18. Analysis element 22 is used to determine the presence or amount of at least one analyte of interest and the particular features of analysis element 22 are not critical to the invention. Thus, any analyte detection method, sensor, or system suitable for use with the analyte of interest, for example optical or electrochemical sensors known in the art, may be used in analysis element 22. An example of a suitable analysis device is an interference-free biosensor such as that described in U.S. patent application Ser. No. not yet available; Atty Docket Number 5843.US.01, filed Dec. 18, 1995).

Figure 2:
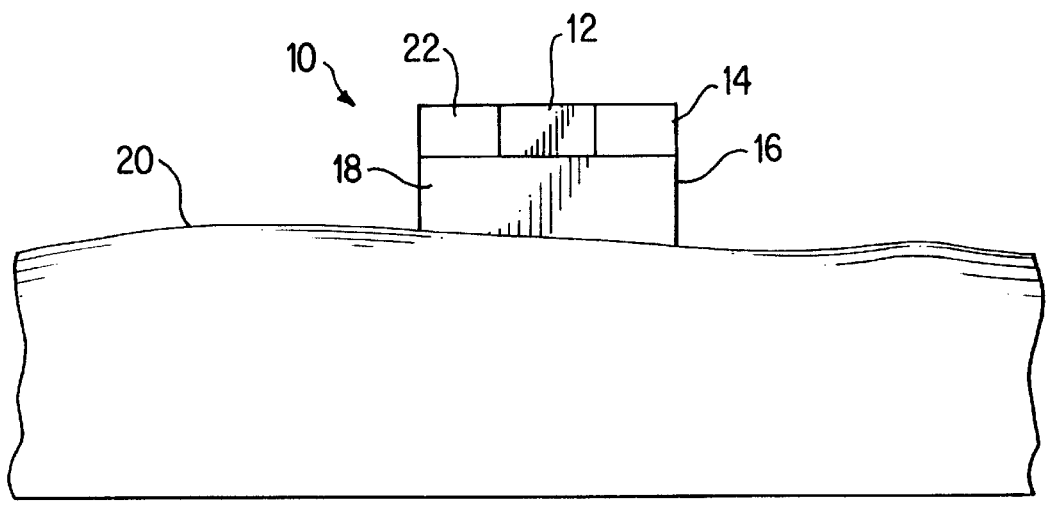
FIG. 2 shows an additional embodiment of the invention.

The operation of a particular embodiment of the invention may be understood with reference to FIG. 2. The ultrasound source 12 generates ultrasonic energy directed at the body surface 20. The transmission of this ultrasonic energy may be facilitated by the use of a coupling medium (such as a gel) within the sampling region 18. The interaction of the ultrasonic energy with the body surface 20 increases the permeability of the skin at the body surface as described in current scientific literature (Mitragotri et al, *J. Pharm. Sci.* 84:697–706, 1995). The pressure reducing, source 14 reduces the pressure in the sampling region 18 by removing air within the region 18. Note that the presence of a coupling medium within the region 18 should not affect the ability of the pressure reducing source 14 to reduce the pressure within the region 18, and may in fact facilitate the pressure reduction by assisting in maintaining a seal between the pressure boundary 16 and the body surface 20. Any coupling medium should as well not interfere with the operation of the analysis device 22. The combination of the enhanced permeability of the skin due to the ultrasonic energy and the pressure difference between the tissue and the sampling region will cause the enhanced flow of body fluid through the body surface 20 into the sampling region, where the concentration of the analyte is measured by the analysis device 22.

Figure 3:
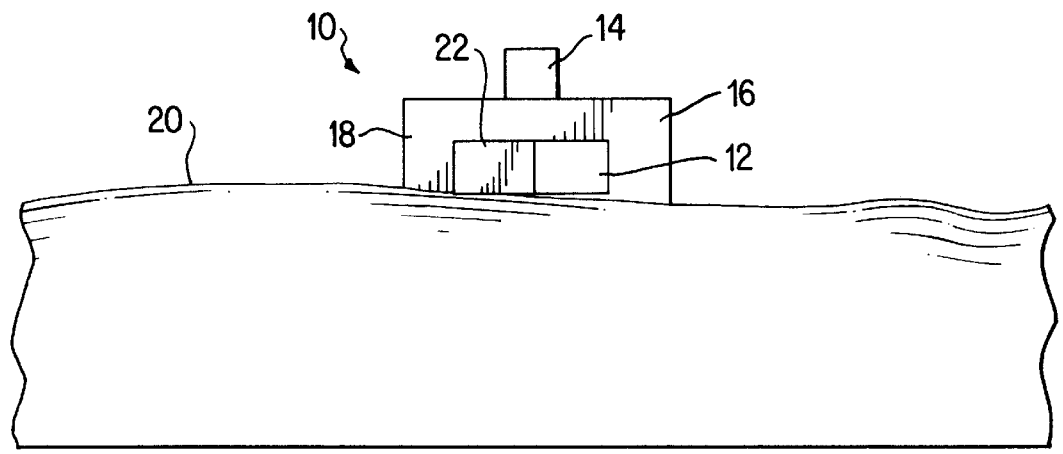
FIG. 3 shows an additional embodiment of the invention.

A second embodiment of the invention is illustrated in FIG. 3. In this embodiment pressure reducing source 14 is in vacuum connection with the pressure boundary 16 and the ultrasound source 12 and the analysis device 22 are contained within the sampling region 18. Such an arrangement facilitates ultrasound transmission, as the ultrasound source 12 may be directly coupled to the body surface 20, if necessary with the local application of a coupling medium such as a gel. This arrangement also facilitates the measurement of the analyte, as the analysis device 22 is not affected by the coupling medium and may directly sense body fluid emerging from the body surface 20.

Figure 4:
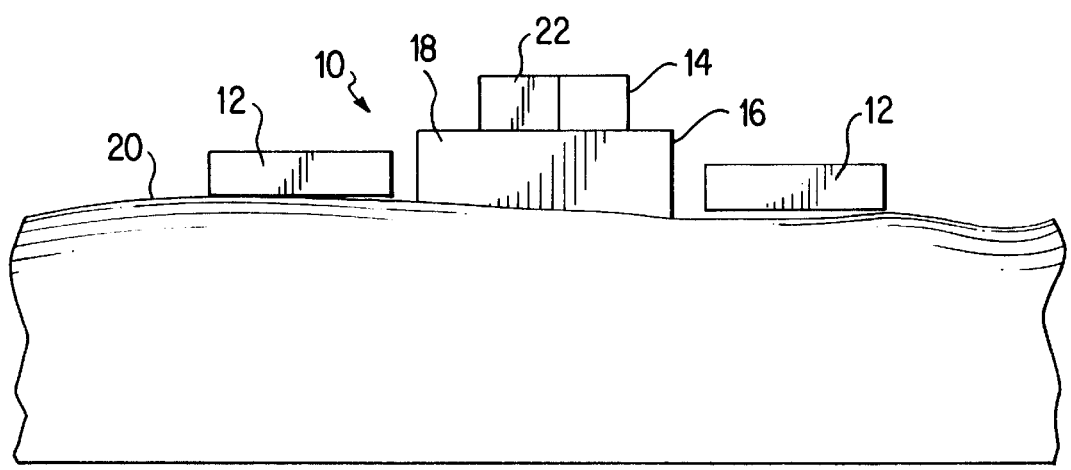
FIG. 4 shows an additional embodiment of the invention.

A third embodiment is illustrated in FIG. 4. Two or more ultrasound sources 12 are placed on opposite sides of the pressure boundary 16, so that they create a standing wave such as that described in U.S. patent application Ser. No. not yet available; Atty Docket Number 5867.US.01, filed Feb. 23, 1996) in the body surface 20 adjacent to the sampling region 18. The reduced pressure source 14 reduces the pressure in the sampling region 18. The combination of the ultrasound enhanced permeability of the skin and the difference in pressure between the tissue and the sampling region 18 causes fluid to exude from the body surface 18. The concentration of the analyte of interest may then be measured by the analysis device 22.

All of the references cited in this application are incorporated by reference. The present invention has been described with reference to preferred and/or alternate embodiments. One of skill in the art will readily appreciate that changes, alterations or modifications can be made to these embodiments without departing from the true scope and spirit of the invention.

We claim:

1. A process of sampling extracellular fluid from an animal having skin comprising the steps of:
    (a) applying ultrasound to a region of the skin of the animal,
    (b) applying reduced pressure at or near the region of the skin where ultrasound has been applied, and
    (c) collecting extracellular fluid from the animal;
    wherein steps (a) and (b) are performed either sequentially or simultaneously.

2. The process of claim 1 wherein the ultrasound is a standing, wave.

3. The process of claim 1 further comprising the step of analyzing tile extracellular fluid for the presence or amount of an analyte.

4. The process of claim 3 wherein the analysis is performed by optical or electrochemical methods.

5. The process of claim 4 wherein the analyte is glucose.

6. An apparatus for sampling extracellular fluid from an animal having skin comprising:
    (a) means for generating an ultrasonic wave through the skin of the animal, said means capable of generating an ultrasonic wave at a region on an external surface of the skin of the animal;
    (b) means for applying reduced pressure to the external surface of the skin of the animal at or near the region on the external surface of the skin where the ultrasonic wave is generated; and
    (c) means for collecting the extracellular fluid that transudes the skin of the animal.

7. The apparatus of claim 6 wherein the ultrasonic wave is a standing wave.

8. The apparatus of claim 6 further comprising an analysis element to analyze the extracellular fluid for the presence or amount of an analyte.

9. The apparatus of claim 8 wherein the analysis is performed by optical or electrochemical methods.

10. The apparatus of claim 9 wherein the analyte is noclucose.

11. In an apparatus for sampling extracellular fluid from an animal having skin comprising:
    a) an ultrasound transducer directed to apply an ultrasonic wave to a region on an external surface of the skin of the animal;
    b) an absorbent material positioned to absorb fluid that transudes the skin of the animal;
    c) means for analyzing the fluid for the presence or amount of analyte;
    the improvement comprising a means for applying reduced pressure to the external surface of the skin at or near
    the region where the ultrasonic wave is applied.

* * * * *

UNITED STATES PATENT AND TRADEMARK OFFICE
CERTIFICATE OF CORRECTION

PATENT NO. : 6,009,343  
DATED : December 28, 1999  
INVENTOR(S) : Eric B. Shain et al.

Page 1 of 1

It is certified that error appears in the above-identified patent and that said Letters Patent is hereby corrected as shown below:

<u>Column 4,</u>  
Line 51, replace "noclucose" with --glucose--.  
Line 26, replace "tile" with --the--.

Signed and Sealed this

Third Day of July, 2001

*Attest:*

NICHOLAS P. GODICI  
*Attesting Officer*     Acting Director of the United States Patent and Trademark Office